(12) United States Patent
Yamashita et al.

(10) Patent No.: US 10,488,180 B2
(45) Date of Patent: Nov. 26, 2019

(54) MASK INSPECTION APPARATUS AND MASK INSPECTION METHOD

(71) Applicant: NuFlare Technology, Inc., Yokohama (JP)

(72) Inventors: Yasuhiro Yamashita, Kanagawa (JP); Riki Ogawa, Kanagawa (JP)

(73) Assignee: NuFlare Technology, Inc., Yokohama (JP)

( * ) Notice: Subject to any disclaimer, the term of this patent is extended or adjusted under 35 U.S.C. 154(b) by 575 days.

(21) Appl. No.: 15/064,204

(22) Filed: Mar. 8, 2016

(65) Prior Publication Data

US 2016/0267648 A1 Sep. 15, 2016

(30) Foreign Application Priority Data

Mar. 9, 2015 (JP) ................................. 2015-046478

(51) Int. Cl.
  *G06T 7/00* (2017.01)
  *G01B 11/00* (2006.01)
  *G01N 21/956* (2006.01)

(52) U.S. Cl.
  CPC ..... *G01B 11/002* (2013.01); *G01N 21/95607* (2013.01); *G06T 7/001* (2013.01);
  (Continued)

(58) Field of Classification Search
  CPC ....... G01B 11/002; G01N 2021/95676; G01N 21/95607; G01N 2201/06113; G01N 2201/12; G06T 2207/10056; G06T 2207/10152; G06T 2207/30148; G06T 5/009; G06T 5/50; G06T 7/001
  (Continued)

(56) References Cited

U.S. PATENT DOCUMENTS

2008/0285840 A1* 11/2008 Kawai ................ G01N 21/8851
  382/141
2010/0098322 A1* 4/2010 Inoue ...................... G06T 7/001
  382/144

(Continued)

FOREIGN PATENT DOCUMENTS

JP 62-19704 A 1/1987
JP 2001-281159 A 10/2001
(Continued)

*Primary Examiner* — Jonathan R Messmore
(74) *Attorney, Agent, or Firm* — Oblon, McClelland, Maier & Neustadt, L.L.P.

(57) ABSTRACT

An inspection target is illuminated by an illumination optical unit using a light source. Optical image data of a pattern disposed in the inspection target is acquired by an imaging unit by causing light transmitted or reflected to be incident to a first and second area of a sensor. Reference image data is generated, corresponding to the optical image data, from design data of the pattern. The optical image data is corrected by obtaining a fluctuation of a gradation value of optical image data acquired using light incident to the second area, and correcting a gradation value of optical image data acquired using the light incident to the first area. A line width of the pattern of the corrected data, and a line width error which is a difference between the line widths of corrected data and reference image data are obtained by the line width error obtaining unit.

13 Claims, 8 Drawing Sheets

(52) U.S. Cl.
  CPC .............. *G01N 2021/95676* (2013.01); *G01N 2201/06113* (2013.01); *G01N 2201/12* (2013.01); *G06T 2207/10152* (2013.01); *G06T 2207/30148* (2013.01)

(58) Field of Classification Search
  USPC .......................................................... 348/87
  See application file for complete search history.

(56) References Cited

U.S. PATENT DOCUMENTS

| | | | | |
|---|---|---|---|---|
| 2011/0091099 | A1* | 4/2011 | Akiyama | G03F 1/84 382/162 |
| 2011/0249112 | A1* | 10/2011 | Endo | G01N 21/956 348/92 |
| 2012/0154837 | A1* | 6/2012 | Yamazaki | B41J 2/2142 358/1.9 |
| 2014/0111636 | A1* | 4/2014 | Inoue | G01N 21/956 348/92 |
| 2014/0307254 | A1* | 10/2014 | Yamashita | G01N 21/95607 356/237.5 |
| 2015/0212019 | A1* | 7/2015 | Shishido | G01B 15/04 250/307 |
| 2015/0279024 | A1* | 10/2015 | Tsuchiya | G03F 1/84 382/144 |

FOREIGN PATENT DOCUMENTS

| | | |
|---|---|---|
| JP | 2007-93317 | 4/2007 |
| JP | 2010-91552 A | 4/2010 |
| JP | 2013-167608 A | 8/2013 |
| JP | 2014-181966 A | 9/2014 |

\* cited by examiner

MASK INSPECTION APPARATUS AND MASK INSPECTION METHOD

CROSS-REFERENCE TO THE RELATED APPLICATION

The entire disclosure of the Japanese Patent Application No. 2015-046478, filed on Mar. 9, 2015 including specification, claims, drawings, and summary, on which the Convention priority of the present application is based, are incorporated herein in its entirety.

FIELD OF THE INVENTION

The present invention relates to a Mask Inspection Apparatus and a Mask Inspection Method.

BACKGROUND

In a production process of a semiconductor element, an original pattern in which a circuit pattern is formed, that is, a mask or a reticle (hereinafter collectively referred to as a mask) is exposed and transferred onto a wafer by a reduction projection exposure apparatus called a stepper or a scanner. Since production of a Large Scale Integration (LSI) requires a large manufacturing cost, it is crucial to improve the production yield.

A defect of a mask pattern can be cited as a large factor of degradation in the production yield of a semiconductor element. Accordingly, it is important to detect a defect in an inspection process during a mask production process. Further, it is also important to measure a line width (CD) of a pattern formed in a mask, generate a map of a distribution of a difference value (line width error: ΔCD) between the measured value of the line width and the design value of the pattern, and feed back the map to the mask production process.

In the inspection process of the mask, the light from a light source irradiates the mask through an optical unit. The mask is positioned on a stage, and then scanned by light as the mask is moved on the stage. The light reflected by the mask is incident to a sensor through lenses. The inspection for detecting a defect of the mask is then performed based on the optical image data acquired by the sensor.

A laser light source, wherein the emission wavelength is in an ultraviolet region, or a plasma light source excited by a laser light source can be used as the light source of the mask inspection apparatus. Most of these light sources are pulse light sources. On the other hand, a TDI (Time Delay Integration) sensor can be used as the sensor that acquires the optical image of the mask. The TDI sensor can input optical images at high speed and is therefore an appropriate sensor for the mask inspection apparatus if the sensitivity of the TDI sensor, at the ultraviolet region, is adequate.

When a light quantity of the light source is fluctuated, a gradation value of the optical image data is fluctuated, and it is then impossible to accurately measure a line width of a pattern, and impossible to obtain an accurate CD map. Therefore, the data output from the TDI sensor is corrected based on the measurement result by measuring the light quantity of the light source. Furthermore, in order to acquire optical image data having a high resolution, it is necessary to synchronize a moving speed of the stage to timing for acquiring the image on the TDI sensor. Japanese Patent Publication 2007-93317 discloses an inspection apparatus comprising a light quantity detecting device for receiving light from the mask, adjacent to the TDI sensor, thereby acquiring information regarding the light quantity fluctuation of the light source, correcting the detection sensitivity of the TDI sensor from the information, and acquiring information of the speed fluctuation of the stage.

In the conventional method, a photodiode is used as the sensor for detecting a light quantity fluctuation of the light source. However, there is a problem in that the correction of the output fluctuation of the TDI sensor due to the light quantity fluctuation is not adequate, and a correction error occurs because of the difference between a band of a response frequency of the photodiode and a band of a response frequency of the TDI sensor. The present invention has been made in view of the above-mentioned problems. That is, an object of the present invention is to provide a mask inspection apparatus and a mask inspection method that can obtain an accurate line width by decreasing the above-mentioned correction error.

SUMMARY OF THE INVENTION

According to one aspect of the present invention, a mask inspection apparatus includes an illumination optical unit, an imaging unit, a reference image data generating unit, a correcting unit, and a line width error obtaining unit. The illumination optical unit illuminates an inspection target using light emitted from a light source. The imaging unit acquires optical image data of a pattern disposed in the inspection target by causing the light transmitted to the inspection target or reflected by the inspection target to be incident to a sensor. The sensor includes a first area, which the light transmitted to or reflected by the inspection target is incident to, and a second area which the light emitted from the light source, is incident to. The reference image data generating unit generates reference image data, corresponding to the optical image data, from design data of the pattern. The correcting unit acquires a gradation value of the optical image data and corrects the gradation value of the optical image data based on a fluctuation of a light quantity of the light source by obtaining a fluctuation of a gradation value of optical image data acquired using the light incident to the second area, and correcting a gradation value of optical image data acquired using the light incident to the first area. The line width error obtaining unit obtains a line width of the pattern of the corrected optical image data, and obtains a line width error which is a difference between the line width of the corrected optical image data and a line width of a pattern of the reference image data corresponding to the optical image data.

According to another aspect of the present invention, a mask inspection method includes calibrating a sensor, which electrically stores an optical image of an inspection target, converts the optical image to an electric signal, and outputs the electric signal. The sensor includes a first area in which a plurality of pixels are arranged along a pixel direction intersecting perpendicularly to a charged accumulation direction in which a charge is accumulated, and a plurality of sections of pixels are arranged along the accumulate direction, and a second area disposed with the same length as the first area at the end of the sensor in the pixel direction, in order to correspond to the characteristics of the first area of the sensor with the characteristics of the second area of the sensor. The inspection target positioned on a table is illuminated with light emitted from a light source. Optical image data of a pattern disposed in the inspection target is acquired by causing the light transmitted or reflected by the inspection target to be incident to the first area of the sensor. Optical image data is acquired by causing the light emitted from the light source, different to the light for illuminating the inspection target, to be incident to the second area. A gradation value of the optical image data acquired using the light incident to the first area by obtaining a fluctuation of a gradation value of the optical image data acquired using the light incident to the second area is corrected. Reference image data is generated corresponding to the optical image data from design data of the pattern. A line width of the pattern of the corrected optical image data is obtained. A line width error that is a difference between the line width of the corrected optical image data and a line width of the pattern of the reference image data corresponding to the optical image data is obtained.

BRIEF DESCRIPTION OF THE DRAWINGS

A more complete appreciation of the present invention and many of the advantages thereof will be readily obtained as the present invention becomes better understood by reference to the following detailed description when considered in connection with the accompanying drawings, wherein.

DETAILED DESCRIPTION OF THE EMBODIMENT

Figure 1:
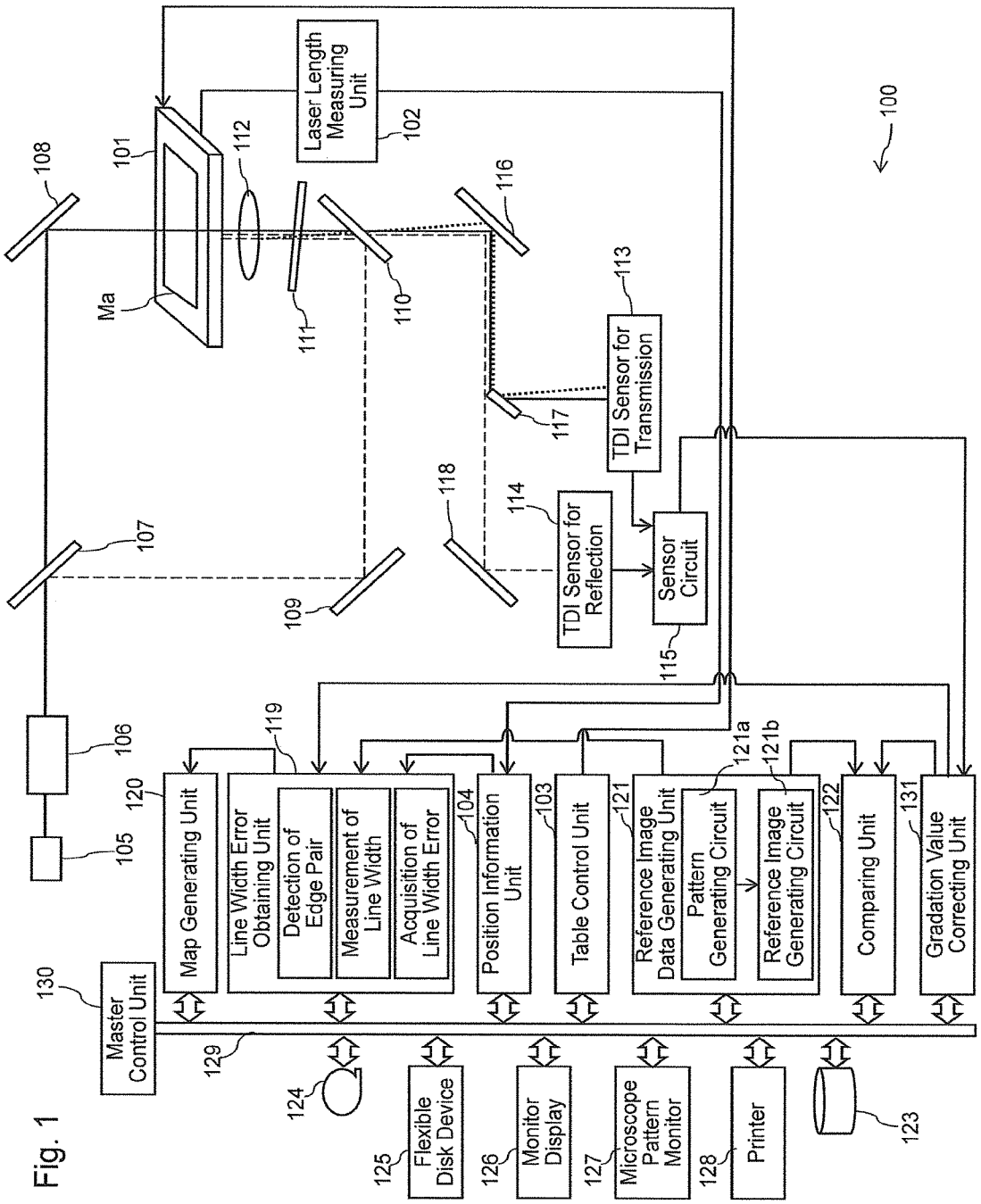
FIG. 1 is a schematic configuration diagram of a mask inspection apparatus according to the present embodiment.

The embodiments will now be described with reference to the accompanying drawings, wherein the same reference numerals designate corresponding or identical elements throughout the various drawings.

FIG. 1 is a schematic configuration diagram of a mask inspection apparatus 100 according to the present embodiment. The mask inspection apparatus 100 obtains optical image data of an inspection target, and then obtains a line width error (ΔCD) of the inspection target using the optical image data to generate a line width error map (ΔCD map). The main constituent components of the mask inspection apparatus 100 are as follows.

The components of the mask inspection apparatus 100, for acquiring optical data of the mask Ma, as one example of the object to be inspected, includes a table 101 that is movable in a horizontal direction (X-direction and/or Y-direction) and a rotation direction (θ-direction), a laser length measuring unit 102 that measures position coordinates of the table 101, an illumination optical unit utilizing a light source 105 that illuminates a mask Ma positioned on the table 101, and an imaging unit that generates optical image data of the mask Ma. In the mask Ma, a pattern, that is an object to be inspected (pattern to be inspected), is formed on a principal surface of a transparent substrate, for example, a glass substrate.

The table 101 is controlled by the table control unit 103. Specifically, the table control unit 103 moves the table 101 in the horizontal direction (X-direction and/or Y-direction) and rotation direction (θ-direction) by driving an X-axis motor, a Y-axis motor, and a θ-axis motor (not shown). For example, an air slider, a linear motor, and a step motor can be used as these driving mechanisms and can further be used in any combination with each other.

The laser length measuring unit 102 is used for measuring the position coordinate of the table 101. Although a detailed illustration of the laser length measuring unit 102 is omitted, it may include a laser interferometer such as a heterodyne interferometer, as one example. The laser interferometer measures position coordinates of the table 101 by illuminating or receiving laser light between each mirror provided along the X-axis and the Y-axis of the table 101. The measured data is sent from the laser length measuring unit 102 to a position information unit 104. A method of measuring the position coordinates of the table 101 is not limited to the method using the laser interferometer, that is, as another example, a method using a magnetic or optical liner encoder can be applied.

The illumination optical unit for illuminating the mask Ma, includes the light source 105, a magnifying optical unit 106, first light dividing unit 107, mirrors 108, 109, 110, second light dividing unit 111, and objective lens 112. If necessary, the illumination optical unit may include a unit for dividing light from the light source 105 into either an optical path for illuminating the mask Ma by transmitting and/or another optical path for illuminating the mask Ma by reflecting, and a unit for changing the illumination light from the light source 105 to a circular polarization light or a linear polarization light etc., and/or an unit for changing the shape of the light source 105 to a point light source shape or a circular light source shape.

A laser light source can be used as the light source 105. For example, a light source emitting DUV (Deep Ultraviolet) radiation can be used.

The light emitted from the laser light source is generally linearly polarized light. According to the present embodiment, the inspection is performed by illuminating the mask Ma to be inspected using linearly polarized light. Thereby, an optical image having a high resolution can be acquired. However, the present embodiment is not limited thereto, and the inspection target can be illuminated by circular polarized light with impartial characteristics, thereby, an optical image with impartial resolution characteristics can be acquired. In order to illuminate the inspection target by the circular polarized light, the light emitted from the light source is transmitted through a quarter-wavelength plate, and then the transmitted light is illuminated to the inspection target.

The first light dividing unit 107 divides a beam of an illumination light emitted from a light source 105 to a light path for illuminating the mask Ma by the transmitted light and another light path illuminating the mask Ma by the reflected light. For example, the first light dividing unit 107 may include a half mirror for reflecting half of the illumination light and for transmitting the other half of the illumination light.

The second light dividing unit 111 divides the light from the light path for illuminating the mask Ma by the reflected light to the transmitted light and the reflected light. The transmitted light illuminates the mask Ma, and the reflected light is incident to the TDI sensor 113 for transmission through the mirrors 110, 116, and 117 without the illumination to the mask Ma.

The first light dividing unit 107 and the second light dividing unit 111 are comprised by covering a thin metal film, for example aluminum, on the transparent substrate, or covering a transparent dielectric layer, called the electric mirror, on the transparent substrate. The partial reflection of the first light dividing unit 107 and the second light dividing unit 111 can be realized by causing the reflected layer to be uniformly transparent or using a total reflection mirror including transparent gaps or holes.

The imaging unit for acquiring the optical image data of the mask Ma includes an imaging optical unit for imaging the optical image of the pattern disposed in the mask Ma by focusing the light transmitted or reflected by the mask Ma; a TDI sensor 113 for transmission for the light transmitted through the mask Ma to be incident thereto, that performs photoelectric conversion on the optical image of the pattern of the mask Ma; a TDI sensor 114 for reflection for the light reflected by the mask Ma to be incident thereto, that performs photoelectric conversion on the optical image of the pattern disposed in the mask Ma; and a sensor circuit 115 that converts an analog signal, output from the TDI sensor 113 for transmission and the TDI sensor 114 for reflection, to a digital signal as optical image data. It is necessary for the imaging unit to generate optical image data of the mask Ma. However, the imaging unit is not limited to the unit described in the present embodiment. Further, it is necessary for the imaging optical unit to acquire the optical image of the pattern disposed in the mask Ma by focusing the light transmitted or reflected by the mask Ma, however, the imaging optical unit is not limited to the unit described in the present embodiment.

An imaging optical unit of the imaging unit includes an objective lens 112, a second light dividing unit 111, a mirror 110, and mirrors 116, 117, 118. The objective lens 112, the second light dividing unit 111, and the mirror 110 are commonly used as an illumination optical unit.

The TDI sensor 113 for transmission and the TDI sensor 114 for reflection electrically store a weak expanded optical image of the mask Ma obtained by the imaging optical unit, and convert the optical image to an electric signal of the image and then output the electric signal. The TDI sensor 113 for transmission and the TDI sensor 114 for reflection are area sensors of which an exposure area can be divided into N-sections. The N-sections are provided along the integration direction for accumulating a charge, that is, in order to acquire an optical image of the mask Ma, when the TDI sensor 113 for transmission and the TDI sensor 114 for reflection are scanning the mask Ma, a charge is transferred in every step along the integration direction and the charges corresponding to several accumulated sections are stored and output. Thereby, even if a charge of one section is weak, the output can be obtained by the accumulation of several sections, that is, the addition of sections, wherein the output corresponds to several tens of the light quantity in the case where the addition is not performed, by the same scan time as the time in the case where the addition is not performed. Furthermore, the noise is decreased and the S/N ratio of the image signal is higher by accumulating the same position several times.

Figure 2:
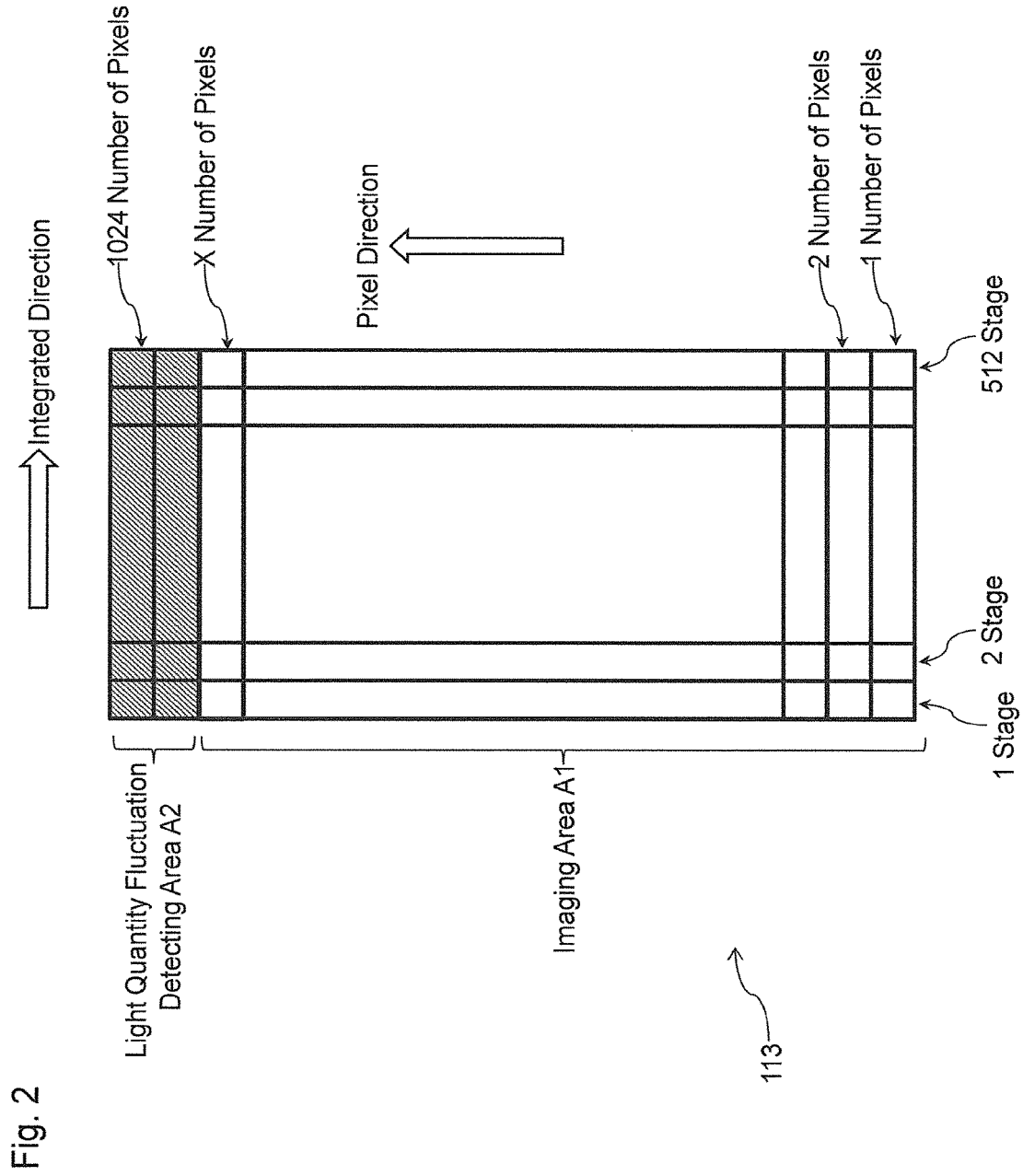
FIG. 2 is a diagram explaining one example of the operation of the TDI sensor for transmission according to the present embodiment.

FIG. 2 is one example of the drawing explaining the operation of the TDI sensor 113 for transmission. In FIG. 2 the pixel direction is the direction intersecting perpendicularly to the integration direction.

In the present embodiment the optical image of the pattern disposed in the mask Ma is acquired by the TDI sensor 113 for transmission, and the fluctuation of the light quantity of the light source 105 is detected using a part of a pixel of the TDI sensor 113 for transmission, then the gradation values of the optical image of the mask Ma acquired by the TDI sensor 113 for transmission are corrected. Thereby, the TDI sensor 113 for transmission includes a first area (hereinafter called the imaging area A1) for acquiring an optical image of the mask Ma, and a second area (hereinafter called the light quantity fluctuation detecting area A2) for detecting the light quantity fluctuation of the light source 105 as shown in FIG. 2. The light quantity fluctuation detecting area A2 having the same length as the imaging area A1 along the integration direction is provided at the end of the pixel direction intersecting perpendicularly to the integration direction.

According to the example shown in FIG. 2, 1024 pixels are arranged along the pixel direction, and 512 sections of pixels are arranged along the integration direction. Among these pixels the area where x pixels are arranged along the pixel direction, and 512 sections of pixels are arranged along the integration direction is the imaging area A1, and the area where (1024-x) pixels are arranged along the pixel direction, and 512 sections of pixels are arranged along the integration direction, is the light quantity fluctuation detecting area A2. The value of x can be set depending on the situation, however the inspection time becomes longer by decreasing the imaging area A1. Therefore, it is preferable to set the value of x so that the area of the light quantity fluctuation detecting area A2 is large enough for detecting the fluctuation of the light quantity and small enough to not increase the inspection time. Regardless of the number of pixels used by the imaging area A1, any remaining pixels not used by the imaging area A1 of the whole area will be used by the light quantity fluctuation detecting area A2. In other words, of the whole area, any pixel not used by area A1 will be used by area A2, and vice versa.

According to the example shown in FIG. 2, in the imaging area A1 and the light quantity fluctuation detecting area A2, pixel information corresponding to 1024 pixels arranged along the pixel direction is simultaneously acquired and charges are transferred in the integration direction. Specifically, an optical image is acquired, at the same position of the pattern, in a pixel of the neighboring sensor element, by moving the table 101, on which the mask Ma is positioned, in the left direction, relative to the TDI sensor 113 for transmission of FIG. 2. At that time, the optical image is acquired by synchronizing the moving speed of the table 101 with the storage time of the TDI sensor 113 for transmission. According to this construction, each image information in both the imaging area A1 and the light quantity fluctuation detecting area A2 are simultaneously acquired by the sensor elements arranged along the image direction. That is, when the gradation value of the optical image acquired at the imaging area A1 is fluctuated, the light quantity fluctuation of the light source causing the fluctuation of the gradation value can be obtained at approximately the same time as the acquisition of the optical image.

As mentioned above, the photodiode is used as a sensor for detecting a light quantity of a light source in the conventional method. However, a difference between the output timing of the photodiode and the output timing of the TDI sensor occurs by the delay of the photodiode, thereby the light quantity signal corresponding to the output of the TDI sensor is output from the photodiode after the output by the TDI sensor. Therefore, when the output value of the TDI sensor is corrected, the correction is performed based on the light quantity output from the photodiode at the same time as the output of the TDI sensor, that is, the light quantity measured before the optical image is acquired by the TDI sensor, and as a result there is a problem in that the correction error occurs.

On the other hand, according to the present embodiment as mentioned above, the light quantity fluctuation of the light source 105 is detected using a group of pixels of the TDI sensor 113 for transmission, therefore it is not necessary to consider the difference between output timings in the conventional method using a photodiode. Therefore, the accurate CD map can be obtained by accurately correcting the output value by the TDI sensor.

In the present embodiment, the output value of the TDI sensor 114 for reflection can be also corrected based on a fluctuation value of a light quantity detected by the TDI sensor 113 for transmission. Further, the light quantity fluctuation can be detected using a group of pixels of the TD1 sensor 114 for reflection. In this case, the fluctuation value of the light quantity can be detected by the TDI sensor 114 for reflection instead of the TDI sensor 113 for transmission, or by the TDI sensor 114 for reflection with the TDI sensor 113 for transmission, and each output value of the TDI sensor 113 for transmission and the TDI sensor 114 for reflection can be corrected based on the obtained fluctuation value.

The mask inspection apparatus 100 includes a gradation value correcting unit 131 as a component for correcting a gradation value of optical image data output from the sensor circuit 115. Furthermore, the components of the mask inspection apparatus 100 also include, for generating a ΔCD map by obtaining a line width error using the optical image data in which the gradation value is corrected, a line width error obtaining unit 119, map generating unit 120, reference image data generating unit 121, magnetic disk device 123 as an example of a storage device, magnetic tape device 124 as an example of an auxiliary storage device, flexible disk device 125 to be another example of the auxiliary storage device, monitor display 126 as an example of a display device, microscope pattern monitor 127 by an ITV camera as another example of a display device, and printer 128. Each component is connected to the master control unit 130 controlling the whole of the mask inspection apparatus 100 through the bus 129 that constitutes a data transmission line. Further, the above-mentioned the table control unit 103 and the position information unit 104 are also connected to the master control unit 130 through the bus 129.

The mask inspection apparatus 100 further includes a comparing unit 122 as a part for determining the existence of a defect of the mask Ma based on the acquired optical image data. Thereby, the existence of the defect of the mask Ma can be obtained while the line width error is obtained, and a ΔCD map is then generated. However, the comparing unit 122 does not necessarily need to be included in the mask inspection apparatus 100. In the case where the comparing unit is provided, the comparing unit compares the optical image data with the reference image data, and determines the existence of a defect in the case when a difference value between the optical image and the reference image is larger than a predetermined threshold value.

Next, an example of a mask inspection method using the mask inspection apparatus 100 shown in FIG. 1 will be described.

Figure 3:
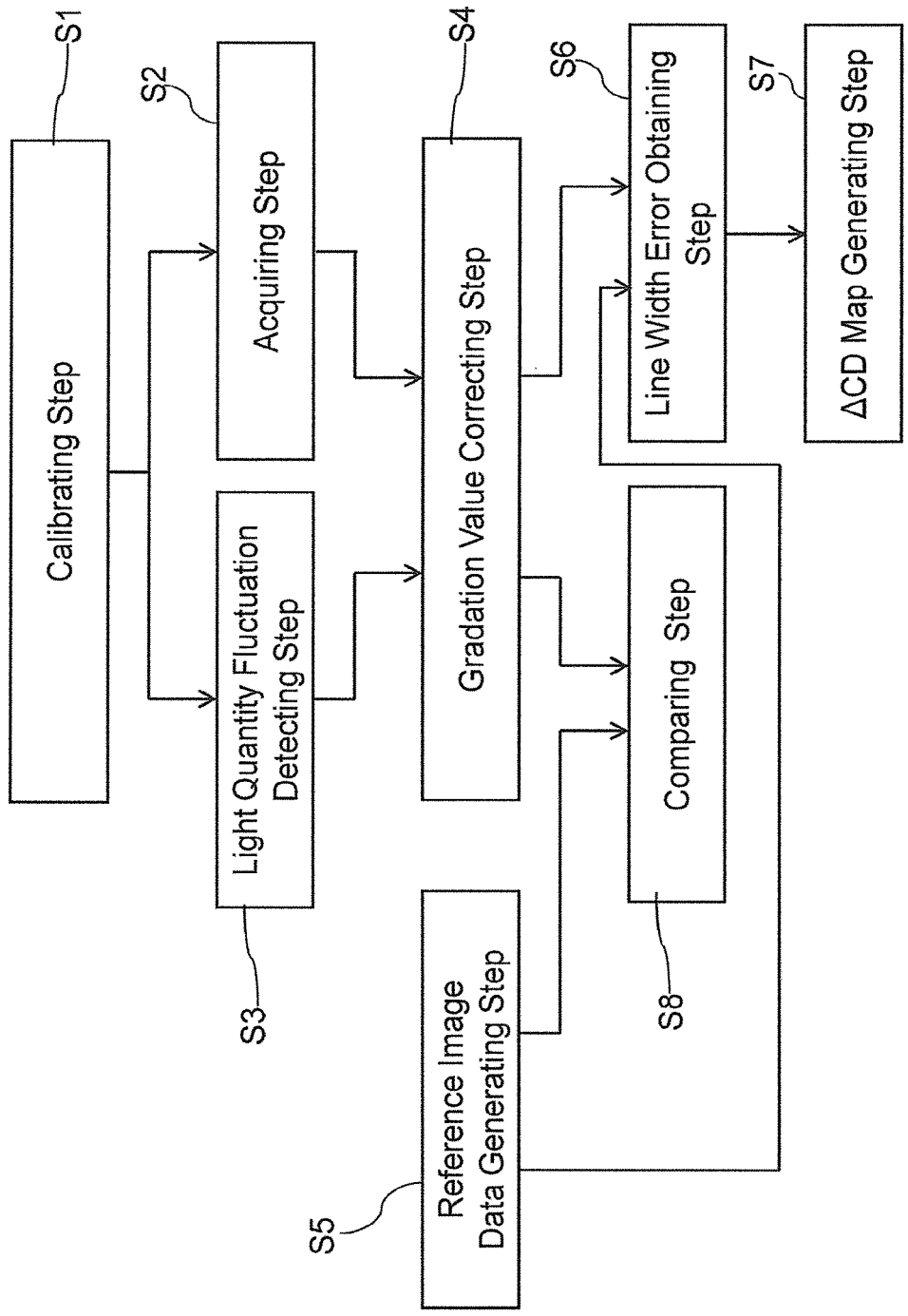
FIG. 3 is one example of a flow chart showing the mask inspection method according to the present embodiment.

FIG. 3 illustrates an example of a flow chart illustrating the mask inspection method according to the present embodiment. As shown in FIG. 3, the mask inspection method according to the present embodiment includes a calibrating step (S1), an acquiring step (S2), a light quantity fluctuation detecting step (S3), a gradation value correcting step (S4), a reference image data generating step (S5), a line width error obtaining step (S6), and a ΔCD map generating step (S7). Further, the mask inspection method according to the present embodiment prefers to include the comparing step (S8) as shown in FIG. 3. These steps will be described using FIG. 1.

<Calibrating Step (S1)>

The TDI sensor is constructed by gathering multiple sensor elements. All sensor elements need to have the same electrical characteristics (gain and offset characteristics) because the fluctuation of the characteristics among these sensor elements causes malfunction. Further, the TDI sensor 113 for transmission according to the present embodiment includes the area (imaging area A1) for acquiring the optical image of the mask Ma, and the area (light quantity fluctuation detecting area A2) for detecting the light quantity fluctuation of the light source 105, and corrects the gradation value of the acquired optical image acquired at the imaging area A1 based on the fluctuation value of the light quantity detected at the light quantity fluctuation detecting area A2. Therefore, it is important that the characteristics of the sensor at the imaging area A1 correspond with the characteristics of the sensor at the light quantity fluctuation detecting area A2. The TDI sensor 113 for transmission is therefore calibrated before the optical image data for the inspection is acquired. The calibration will be specifically explained below.

The optical image acquired by the TDI sensor 113 for transmission is input to a digital amplifier (not illustrated), provided in the sensor circuit 115, which can adjust an offset and a gain of each pixel. Specifically, the calibrating step is a step for determining the gain of each pixel of the digital amplifier. For example, in the calibrating process step for calibrating the TDI sensor 113 for transmission, the TDI sensor 113 for transmission is positioned at the area where the light is transmitted through the mask Ma, sufficiently wider than an area in which the optical image is acquired by the imaging unit. Next, the optical image of the mask Ma is acquired under the same conditions (for example, the same output of the light source, light quantity of the light source, positions of the various mirrors and lenses, etc) of the illumination optical unit for irradiating the mask Ma during the inspection, and then a gradation value (I_img_hi) of the optical image acquired in the imaging area A1, and a gradation value (I_sens_hi) of the optical image acquired in the light quantity fluctuation detecting area A2 are obtained to determine a white level. After the light quantity of the light for irradiating the mask Ma is set to zero, a gradation value (I_img_zero) of the optical image acquired in the imaging area A1, and a gradation value (I_sens_zero) of the optical image acquired in the light quantity fluctuation detecting area A2 are obtained to determine a black level. At this point, in consideration of a fluctuation in light quantity during the inspection, the offset and gain are adjusted in each pixel such that amplitudes of the white level and black level are distributed in a range of 10 to 240 corresponding to approximately 4% to approximately 94% of 8-bit gradation data. Each obtained gradation value (I_img_hi, I_sens_hi, I_img_zero, and I_sens_zero) is stored in the magnetic disk device 123 shown in FIG. 1.

The optical image data acquired by the TDI sensor 114 for reflection is also input to a digital amp of the sensor circuit 115, and the gain of each pixel of the digital amp is determined by the calibration.

<Acquiring Step (S2)>

The optical image of the pattern disposed in the mask Ma is acquired in the acquiring step S2 performed after the calibrating step S1.

Firstly, the mask Ma is positioned on the table 101. The mask Ma is fixed on the table 101 using a vacuum pump, for example. To accurately perform the measurement of the line width of the pattern formed in the mask Ma, it is necessary that the pattern disposed in the mask Ma as a measurement target is adjusted to the predetermined position on the table 101. For example, an alignment mark can be provided to align the pattern disposed in the mask Ma on the table 101. An optical image of the alignment mark is acquired by the mask inspection apparatus 100, and then the table 101, on which the mask Ma with the pattern disposed therein is positioned, is adjusted to the predetermined position using the optical image of the alignment mark, acquired by the mask inspection apparatus 100. Further, when the mask Ma is placed at the predetermined position on the table 101 provided in a mask inspection apparatus, a rotation angle (θ) from the predetermined position of the mask Ma or whole extension and contraction of the pattern due to a temperature can be calculated using the alignment mark. For example, XY-coordinate axes of the pattern surface of the mask Ma are aligned parallel and perpendicular to a traveling axis of the table 101 in the mask inspection apparatus. Thereby a rotation error or an extension and contraction error of the pattern disposed in the mask Ma is normalized with respect to the optical unit of the mask inspection apparatus 100. For example, X-axes and Y-axes of the two alignment marks that are provided in the mask Ma to establish a horizontal or vertical position relationship are adjusted so as to be parallel or perpendicular to the traveling axis of the table 101, the mask Ma is adjusted so as to be located at the predetermined position by rotating a θ-axis of the table 101 based on the alignment mark, and a distance between the two alignment marks is measured. An extension and contraction ratio of the mask Ma is calculated by comparing the measured distance to a theoretical distance between the alignment marks, which is previously provided to the mask inspection apparatus 100. Accuracy of a measurement value can be enhanced by reflecting the obtained value on the correction of the measurement value of the position or dimension of the pattern.

As one example, a plurality of mask alignment marks MA having a cross shape are formed at different position to the region where the pattern to be inspected of the mask Ma is formed. Further, a plurality of chip patterns are formed in the mask Ma, and chip alignment marks CA are formed in each chip. The table 101 includes a XY-table movable along the horizontal direction, and a θ-table movable in the rotation direction on the XY-table. Specifically, in the alignment process, an X-axis and a Y-axis of the pattern to be measured are aligned with the running axis of the XY-table while the mask Ma is positioned on the table 101.

The mask alignment mark MA does not necessarily need to be provided in the mask Ma. In this case, the alignment can be performed using the vertex of the corner, in which the X-coordinate and Y-coordinate are equal, or the side of the edge pattern, which is close to an outer periphery of the mask Ma, in the pattern disposed in the mask Ma.

When the mask Ma is positioned on the table 101 at the predetermined position, the pattern formed in the mask Ma is irradiated with the light from the illumination optical unit. Specifically, the light from the light source 105 irradiates the mask Ma through the magnifying optical unit 106. Then, the illumination light transmitted or reflected by the mask Ma is focused by the imaging optical unit to be incident to the TDI sensor 113 for transmission and the TDI sensor 114 for reflection, and thereby an optical image of the pattern disposed in the mask Ma is acquired.

More specifically, as shown in the light path as illustrated by the solid line of FIG. 1 the light emitted from the light source 105 transmits through the magnifying optical unit 106, and the light path of the light is then divided by the first light dividing unit 107. The light path of the light transmitted through the first light dividing unit 107 is bent by the mirror 108, and then illuminates the mask Ma. Then, the light illuminated to the mask Ma transmits through the mask Ma, and then transmits through the objective lens 112, the second light dividing unit 111, and the mirror 110, in this order, and is then incident to the TDI sensor 113 for transmission through the mirrors 116 and 117. Thereby, the transmission optical image of the pattern disposed in the mask Ma is acquired. As mentioned above, the TDI sensor 113 for transmission according to the present embodiment includes the imaging area A1 and the light quantity fluctuation detecting area A2 and the light transmitted through the mask Ma is incident to the imaging area A1, and the optical image of the pattern disposed in the mask Ma is acquired by the light incident to the imaging area A1.

On the other hand, as shown in the light path illustrated by the broken line of FIG. 1, the light reflected by the first light dividing unit 107 transmits through the second light dividing unit 111, the objective lens 112 via the mirror 109, the mirror 110, and then illuminates to the mask Ma. The light illuminated to the mask Ma is reflected by the mask Ma and then transmits through the objective lens 112, the second light dividing unit 111, and the mirror 110 in this order, and is then illuminated to the TDI sensor 114 for reflection via the mirror 116 and the mirror 118. Thereby, the reflection optical image of the pattern disposed in the mask Ma is acquired. The mirror 110 is a half mirror and as mentioned above the light transmitted through the mask Ma transmits through the mirror 110 and is then incident to the imaging unit, and the light from the mirror 109 is reflected by the mirror 110 and then illuminates to the mask Ma. The combination of a polarized beam splitter and an optical element which can change the polarized plate of the linearly polarized light emitted from the light source 105 can be used instead of the mirror 110.

A method for acquiring the optical image of the pattern disposed in the mask Ma using the TDI sensor 113 for transmission and the TDI sensor 114 for reflection is as follows. In the explanation for the acquiring method the TDI sensor 113 for transmission is not distinguished with the TDI sensor 114 for reflection, and both sensors are referred to as a TDI sensor.

A region to be inspected in the mask Ma, that is, the region in which a pattern to be inspected is formed is virtually divided into the stripe-shaped multiple regions. The stripe-shaped region is called a stripe. Each stripe-shaped region has, for example, a width of several hundred micrometers and a length of about 100 mm that corresponds to a total length in an X-direction or a Y-direction of the region to be inspected.

Further, a plurality of units, each unit represented by "F", in which optical images are acquired (hereinafter each unit is referred to as "frame"), are divided in a grid shape virtually set in each stripe. Each frame is preferably a square having each side equal to the width of the stripe, or a square, wherein each side of the square is the width of the stripe divided into approximately four, that is, the perimeter of the square is equal to the width of the stripe.

Figure 4:
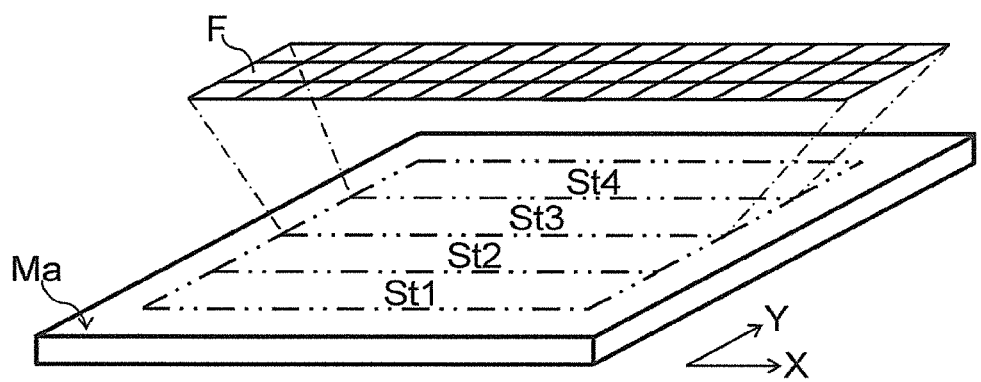
FIG. 4 is a schematic diagram for explaining the relationship between the stripes and the frames, and the region to be inspected of the mask.

FIG. 4 is a schematic diagram explaining a relationship between the area to be inspected of the mask Ma, and stripes and frames. In this example, the region to be inspected is hypothetically divided by four stripes ST1 to ST4. Furthermore, in each stripe ST1 to ST4, 45 frames are hypothetically set.

Each stripe ST1 to ST4 has a long shape extending along the X-direction and are arranged along the Y-direction. On the other hand, each frame includes a rectangular shape, for example, a length of one side is several tens of micrometers. In this case, in order to acquire the complete optical image, that is, to prevent the leakage of acquiring the optical image between two frames adjacent frames, the edge of one frame is positioned so that the edge is overlapped to the edge of another frame by a predetermined width. The predetermined width can be a width corresponding to 20 pixels of the TDI sensor, for example. The edges of the adjacent stripes are set so that the edges overlapped each other in the same manner as the frames.

Next, the optical image of the mask Ma is acquired in each stripe. That is, in acquiring the optical image as shown in FIG. 4, the operation of the table 101 is controlled such that each stripe $St_1$, $St_2$, $St_3$, $St_4$, . . . is continuously scanned. Specifically, the optical image of the stripe $St_1$ is sequentially acquired along X-direction while the table 101 is moved in the −X-direction as shown in FIG. 4. The optical image is continuously input to the TDI sensor. The optical image of the stripe $St_2$ is acquired after the optical image of the stripe $St_1$ is acquired. In this case, after the table 101 moves in the −Y-direction in a stepwise manner, the optical image is acquired while the table 101 moves in the direction (X-direction) opposite to the direction (−X-direction) in which the optical image of the stripe $St_1$ is acquired, and the optical image of the stripe $St_2$ is continuously input to the TDI sensor. When the optical image of the stripe $St_3$ is acquired, after moving the table 101 in the −Y-direction in the stepwise manner, the table 101 moves in the direction opposite to the direction (X-direction) in which the optical image of the stripe $St_2$ is acquired, namely, the direction (−X-direction) in which the optical image of the stripe $St_1$ is acquired. The optical image of the stripe St4 is acquired in the same manner as mentioned above.

After the TDI sensor 113 for transmission and the TDI sensor 114 for reflection acquire the optical images of the pattern disposed in the mask Ma, analogue signals corresponding to the acquired optical images are sequentially output to the sensor circuit 115. The sensor circuit 115 converts each analogue signal, output from the TDI sensor 113 for transmission and the TDI sensor 114 for reflection, to digital signals as optical image data to be the optical image data. The optical image data is output from the sensor circuit 115 to the line width error obtaining unit 119 and the comparing unit 122.

<Light Quantity Fluctuation Detecting Step (S3)>

In the light quantity fluctuation detecting step S3 the light quantity fluctuation of the light source 105 is detected using a group of pixels of the TDI sensor 113 for transmission. Specifically, this step is a step for acquiring optical image data at the light quantity fluctuation detecting area A2 of the TDI sensor 113 for transmission. This step is performed parallel with the step for acquiring the optical image of the pattern disposed in the mask Ma by the TDI sensor 113 for transmission.

As mentioned in the acquiring step S2, after the light emitted from the light source 105 transmits through the magnifying optical unit 106, it is reflected by the first light dividing unit 107, and bent by the mirror 109 to be incident on the mirror 110. Next, the light reflected by the mirror 110 travels to the second light dividing unit 111. Until this point, the light path is the same as the light path of the light for acquiring the reflected optical image of the pattern disposed in the mask Ma.

Most light from the mirror 110 to the second light dividing unit 111 is reflected from the second light dividing unit 111 and reflected by the mask Ma, and as shown in the light path as illustrated by the block line of FIG. 1, a part of the light is reflected by the second light dividing unit 111 and is then returned to the mirror 110. Then, the light transmitted through the mirror 110 is incident to the light quantity fluctuation detecting area A2 of the TDI sensor 113 for transmission by the mirrors 116 and 117. In order for the light reflected by the second light dividing unit 111 to be incident to the TDI sensor 113 for transmission, after travelling on the light path, the second light dividing unit 111 is provided so that it is bent to the optical axis of the light transmitted through the mask Ma or reflected by the mask Ma and to be incident to the mirror 110. That is, if the angle between the second light dividing unit 111 and the optical axis is 90 degrees, the light reflected by the second light dividing unit 111 is incident to the TDI sensor 114 for reflection, therefore the angle is adjusted so that the light is incident to the TDI sensor 113 for transmission.

As mentioned above, the second light dividing unit 111 reflects a part of the incident light. The reflectivity of the second light dividing unit 111 can be set depending on the situation. In the present embodiment the second light dividing unit 111 requires adequate reflectivity for allowing light to be incident to the TDI sensor 113 for transmission, and for detecting the light quantity fluctuation of the light source 105. On the other hand, both the light for acquiring the optical image of the mask Ma, specifically the light to be incident to the TDI sensor 113 for transmission through the mask Ma, and the light to be incident to the TDI sensor 114 for reflection reflected by the mask Ma need to transmit through the second light dividing unit 111. Therefore, the transmission of the second light dividing unit 111 is required to transmit enough light for acquiring the appropriate optical image for inspecting by these sensors.

<Gradation Value Correcting Step (S4)>

A difference between the time elapsing between when the light is emitted from the light source 105, and when the light is incident to the TDI sensor 113 for transmission after the light is transmitted through the mask Ma, and the time elapsing between when the light is emitted from the light source 105, and when the light is incident to the TDI sensor 113 for transmission after the light is divided by the first light dividing unit 107 and is then reflected by the second light dividing unit 111, is negligibly small. Therefore, the fluctuation of the light quantity of the light for acquiring the optical image of the pattern disposed in the mask Ma, can be detected in real time. That is, when the light quantity of the light source 105 is fluctuated, the gradation value of the optical image acquired in the light quantity fluctuation detecting area A2 is fluctuated. The gradation value of the optical image acquired in the imaging area A1 and output with the optical image in the light quantity fluctuation detecting area A2 is corrected depending on the fluctuation amount of the light quantity. Thereby, the line width of the pattern disposed in the mask Ma can be accurately measured.

In the gradation value correcting step S4 shown in FIG. 3, the above-mentioned correction, that is, the correction to the gradation value of the optical image acquired in the imaging area A1 depending on the fluctuation amount of the light quantity of the light source, is performed in the gradation value correcting unit 131 shown in FIG. 1. The specific correction method is described as follows.

The optical image data obtained in the acquiring step S2, and the optical image data obtained in the light quantity fluctuation detecting step S3 are transmitted to the gradation value correcting unit 131.

The gradation value of the optical image data obtained in the acquiring step S2, that is, the gradation value of the optical image acquired in the imaging area A1 of the TDI sensor 113 for transmission, is simplified as (I_img). The gradation value of the optical image obtained in the light quantity fluctuation detecting step S3, that is, the gradation value of the optical image acquired in the light quantity fluctuation detecting area A2 of the TDI sensor 113 for transmission is simplified as (I_sens). The gradation value (I_sens_hi) in the light quantity fluctuation detecting area A2 when the optical image of the mask Ma is acquired by the same illumination condition as the inspection, and the gradation value (I_img_zero) in the imaging area A1 when the light quantity of the light for illuminating the mask Ma is zero, and the gradation value (I_sens_zero) in the light quantity fluctuation detecting area A2, obtained in the calibrating step S1, are read from the magnetic disk device 123. The corrected gradation value (I_corr) of the optical image in the imaging area A1 can be obtained using these gradation values by the following formula.

$$I\_corr = I\_img - I\_img\_zero \times \{(I\_sens - I\_sens\_zero)/(I\_sens\_hi - I\_sens\_zero)\} + I\_img\_zero \quad \text{FORMULA 1}$$

When the light quantity of the light source 105 is not fluctuated, Formula 2 is:

$$I\_sens = I\_sens\_hi \quad \text{FORMULA 2}$$

Therefore, from the above-mentioned Formula 2, Formula 3 is:

$$I\_corr = I\_img \quad \text{FORMULA 3}$$

Accordingly, a correction for the gradation values of the optical image in the imaging area A1 is unnecessary.

<Reference Image Data Generating Step (S5)>

In the reference image data generating step S5 shown in FIG. 3, reference image data is generated based on the design pattern data of the mask Ma in the reference image data generating unit 121 shown in FIG. 1. The reference image data is used for the calculation for the standard line width when the line width error of the pattern disposed in the mask Ma is obtained, in the line width error obtaining step S6. Further, the reference image data is also a standard for the determination of the existence of a defect of the optical image data in the inspection by the die-to-database comparison method in the comparing step S8.

Figure 8:
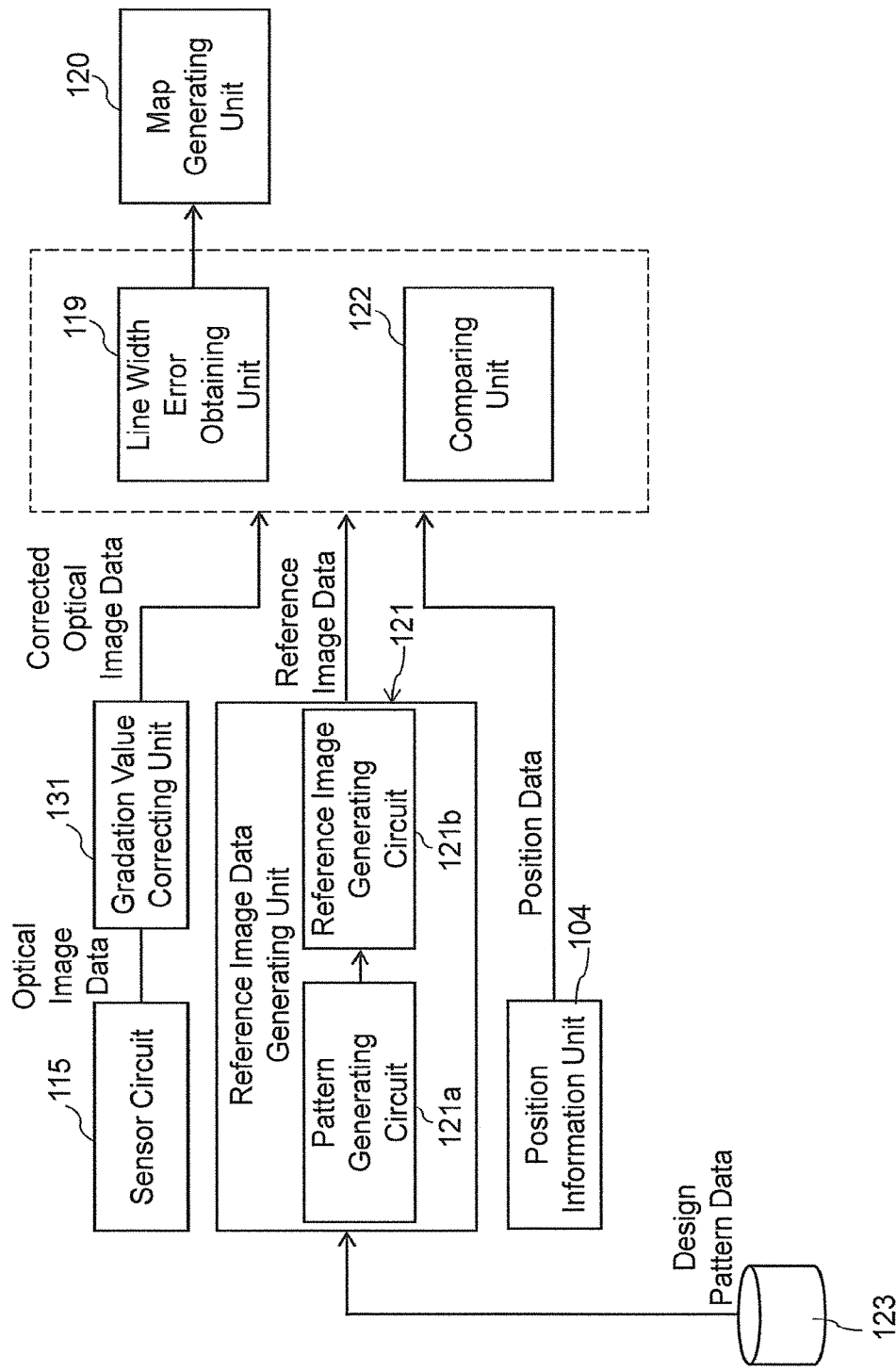
FIG. 8 is a schematic diagram of the flow of data of the mask inspection apparatus according to the present embodiment.

FIG. 8 is a schematic diagram illustrating a flow of data in the mask inspection apparatus 100 shown in FIG. 1. The reference image data generating step S5 will be described referring to FIGS. 1 and 8.

The design pattern data of the mask Ma is stored in the magnetic disk device 123. The design pattern data is read from the magnetic disk device 123, and is then transmitted to the reference image data generating unit 121. The reference image data generating unit 121 includes the pattern generating circuit 121a and the reference image generating circuit 121b. When the design pattern data is input to the pattern generating circuit 121a, the pattern generating circuit 121a converts the design pattern data to a binary or multi-image data. Then, the image data is transmitted from the pattern generating circuit 121a to the reference image generating circuit 121b. In the reference image generating circuit 121b the filter process is performed to the image data. The reason why the filtering process of the image data is performed is as follows.

In the production process, because roundness of a corner and a finished dimension of the line width of the pattern disposed in the mask Ma is generally adjusted, the pattern disposed in the mask Ma does not strictly correspond to with the design pattern. Further, the optical image data output from the sensor circuit 115 is faint due to a resolution characteristic of the magnifying optical unit 106 or an aperture effect of the TDI sensor 113 for transmission and the TDI sensor 114 for reflection, in other words, the functioning state of a spatial lowpass filter.

Accordingly, a function for generating a reference image, hereinafter referred to as a "reference image generating function", is determined by simulating the fluctuation caused by the production process of the mask Ma and the optical unit of the mask inspection apparatus 100 based on the design pattern data and the optical image data of the mask Ma. The design pattern data is subjected to a two-dimensional digital filter using the reference image generating function. According to the present embodiment, the reference image generating circuit 121b performs a filtering process to the image data output from the pattern generating circuit 121a, using the reference image generating function, to generate the reference image data.

<Line Width Error Obtaining Step (S6)>

When the line width (CD) of the pattern formed in the mask Ma is measured, it is necessary for the position of the edge of the pattern as a reference position of the measurement to be determined. In the present embodiment, the position of the edge is determined by a conventionally known threshold value method. For example, an arbitrary value (threshold value) is specified between the signal amount (luminance) of the black level and the signal amount (luminance) of the white level of the reference image data. The threshold value is a value internally divided between the minimum value and the maximum value of the signal amount by a prescribed division ratio. Then, the position of the edge is set at a position corresponding to the signal amount of the threshold value in the reference image data. Further, the position of the edge is set at a position of the signal amount that corresponds to this threshold value in the optical image data. For example, in the case of a line-and-space pattern, a threshold value corresponds to the boundary between the line pattern and the space pattern.

Figure 5:
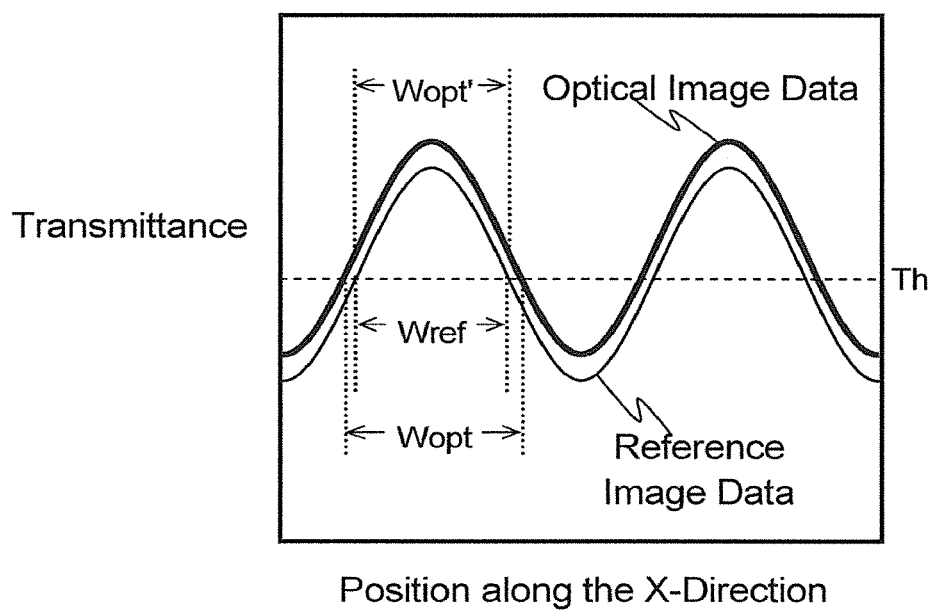
FIG. 5 is one example of the transmittance of the light to be incident to the TDI sensor for transmission according to the present embodiment.

FIG. 5 illustrates an example of the transmittance of light being incident to the TDI sensor 113 for transmission shown in FIG. 1. In FIG. 5, the horizontal axis illustrates a position along the X-direction on the TDI sensor 113 for transmission, and the vertical axis illustrates the transmittance of light. Further, in FIG. 5 the thin line curve illustrates a reference image data.

Figure 6:
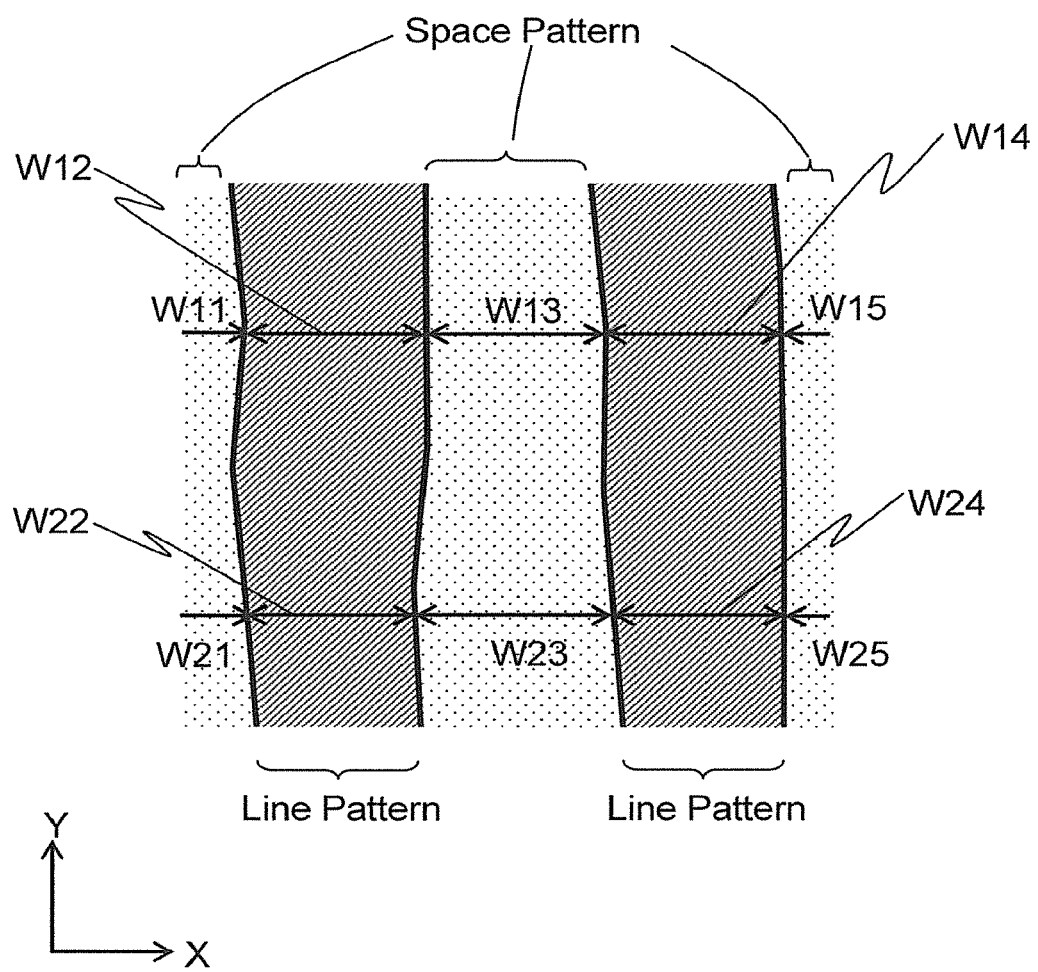
FIG. 6 is a partial plan view of the line-and-space pattern as one example of the pattern to be measured.

The threshold value Th that determines the position of the pattern, is determined from the reference image data, illustrated by the thin line in FIG. 6, using the Formula (4).

$$Th = \{(\text{Maximum Value of Transmittance}) - (\text{Minimum Value of Transmittance})\}/2 \quad \text{FORMULA 4}$$

When the threshold value Th is determined, the position of the edge of the pattern is determined. Accordingly, the line width Wref of the pattern is obtained. The line width Wref corresponds to the design value of the line width of the pattern. The line width error (ΔCD) is obtained by calculating the difference between the line width Wref and the line width of the optical image data corresponding to the actual pattern. In the optical image data, the position of the signal amount (transmittance) equal to the threshold value Th represents the edge of the pattern.

In the case where the pattern is formed in the mask Ma as designed, the optical image data of the pattern should correspond with the reference image data of the pattern. Therefore, the line width of the optical image data should be equal to the line width Wref. However, in the case where the light quantity of the light source 105 shown in FIG. 1 is increased, the signal amount (transmittance) of the optical image data will have the same curve as illustrated by the thick line in FIG. 5. Accordingly, when the position of the edge of the pattern is determined using the threshold value Th in the optical image data, the line width Wopt is obtained, and the line width error (ΔCD: Wopt-Wref) occurs between the line width Wopt and the line width Wref. That is, though the line width of the pattern obtained from the optical image data should be identical to Wref, and the line width error (ΔCD) should be zero, the line width error (Wopt-Wref) occurs. Therefore, a correct line width error cannot be obtained.

On the other hand, in the present embodiment the gradation value of the optical image of the pattern disposed in the mask Ma is corrected depending on the fluctuation amount of the light quantity of the light source 105 in the gradation value correcting step S4. That is, the transmittance of the optical image data is corrected from the curve illustrated by the thick line to the curve illustrated by the thin line. Therefore, the line width of the pattern disposed in the mask Ma becomes Wopt' and the accurate line width error can be obtained.

The line width error is specifically obtained as follows.

Firstly, the optical image data, the gradation value of which is corrected in the gradation value correcting step S4, is transmitted from the gradation value correcting unit 131 to the line width error obtaining unit 119. Using the transmitted optical image data and the reference image data transmitted from the reference image data generating unit 121, an edge pair that is used for the measurement of the line width (CD) is detected. Specifically, a position of the edge of the pattern in the optical image data is determined using the above-mentioned threshold value. Then, a position of the edge of the optical image data that is paired with the position of the edge of the pattern in the reference image data, is detected. The edge pair consists of one edge that becomes a starting point for the measurement of a line width, and another edge that becomes an ending point of the measurement of the line width among the detected edges. As one example, the edge pair is detected in a unit of a pixel. For example, in the case where the pattern is a line pattern consisting of two edges extending along the Y-axis, an edge pair is detected in a unit of a pixel on both edges. Further, in the case where the pattern is a line pattern consisting of two edges extending along the X-axis, an edge pair is also detected in a unit of a pixel on both edges.

The detection of the edge pair is performed in the line width error obtaining unit 119. The measurement value of the position coordinate of the table 101 measured by the laser length measuring unit 102 and is transmitted from the position information unit 104 to the line width error obtaining unit 119. Thereby a position coordinate of each edge is obtained. Specifically, this process will be described as follows. Firstly, optical image data acquired in a unit of a stripe, is divided into data of a predetermined size, for example, data of a unit of a frame. Next, a predetermined region of optical image data is compared with reference image data corresponding to the predetermined region, and then the table 101 is moved in parallel to a position at which an absolute value of a difference between the optical image data and the reference image data becomes the minimum, or a position at which the sum of squares of the difference between the optical image data and the reference image data becomes the minimum, using a pattern corresponding method. A position coordinate of the pattern to be measured is determined from the amount of the parallel movement and from the data of the laser length measuring unit 102 corresponding to the frame. Thereby the position coordinate of the edge can be obtained.

After the edge pair is detected, the line width error is acquired in the line width error obtaining unit 119.

As one example of a pattern to be measured, the pattern is a line-and-space pattern of which each line pattern consisting of two edges extending along the Y-direction that are arranged along the X-direction at predetermined intervals so that a plurality of space patterns are formed. A line width error regarding the line width of the line pattern, and a line width error regarding the line width of the space pattern are individually measured. Specifically, the line widths of each line pattern and the line widths of each space pattern are measured using the detected edge pairs.

FIG. 6 is a plan view of a part of a line-and-space pattern as an example of a pattern to be measured. In FIG. 6, the part indicated by the hatched lines corresponds to the line pattern, the section provided between two line patterns corresponds to the space pattern. For example, the line widths W12, and W14, etc., are measured along the X-direction at the same position of the Y-direction in regards to each line pattern. In the same manner, the line widths W11, W13, and W15, etc., are measured along the X-direction in regards to each space pattern. Then, at the next position shifted by one pixel in the –Y-direction, the line widths W22, and W24, etc., are measured along the X-direction at the same position of the Y-direction in regards to each line pattern. In the same manner, the line widths W21, W23, and W25, etc., are measured along the X-direction in regards to each space pattern.

Figure 7:
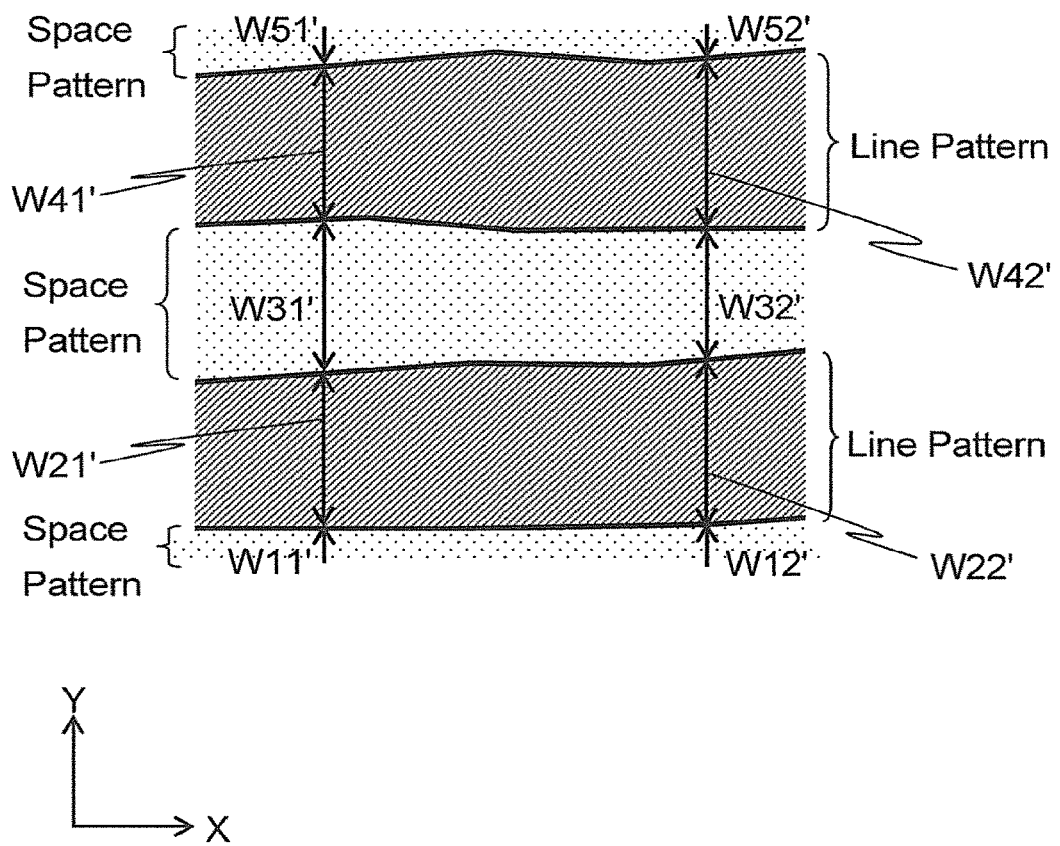
FIG. 7 is another partial plan view of the line-and-space pattern as one example of the pattern to be measured.

FIG. 7 also is a plan view of a part of a line-and-space pattern. In FIG. 7, the section indicated with the hatched lines corresponds to the line pattern, and the section provided between two line patterns corresponds to the space pattern in the same manner as FIG. 6. As shown in FIG. 7, the pattern is a line-and-space pattern of which each line pattern consisting of two edges extending along the X-direction, are arranged along the Y-direction at predetermined intervals so that a plurality of space patterns are formed. In this case, a line width error regarding the line width of the line pattern, and a line width error regarding the line width of the space pattern are also measured individually. That is, the line widths of each line pattern and the line widths of each space pattern are measured using the detected edge pairs.

Specifically, the line widths W21', and W41', etc., are measured along the Y-direction at the same position of the X-direction in regards to each line pattern. In the same manner, the line widths W11', W31', and W51', etc are measured along the Y-direction in regards to each space pattern. Then, at the next position shifted by one pixel in the X-direction, the line widths W22', and W42', etc are measured along the Y-direction at the same position of the X-direction in regards to each line pattern. In the same manner, the line widths W12', W32', and W52', etc are measured along the Y-direction in regards to each space pattern.

These line widths measured by the above-mentioned method in regards to each pattern are compared to line widths obtained using edge pairs of the reference image data corresponding to these edge pairs of the optical image data to obtain the difference. The obtained difference is a line width error. The line width error is obtained in each frame, for example. In the example shown in FIG. 6, and the example shown in FIG. 7, the line width errors along the X-direction, and the line width errors along the Y-direction are obtained, using the measurement values, in each frame in regards to the line pattern. In the same manner, the line width errors along the X-direction, and the line width errors along the Y-direction are obtained, using the measurement values, in each frame in regards to the space pattern.

<$\Delta$CD Map Generating Step (S7)>

The $\Delta$CD map generating step (S7) shown in FIG. 3, is performed in the map generating unit 120 shown in FIG. 1. Specifically, the value of the line width error ($\Delta$CD) and the measurement value of the position coordinate of the table 101 (transmitted from the position information unit 104) are transmitted from the line width error obtaining unit 119 to the map generating unit 120. The map generating unit 120 generates a $\Delta$CD map by associating the line width error ($\Delta$CD) with the position coordinate on the mask Ma.

For example, a whole pattern to be measured is divided into a plurality of unit regions consisting of a predetermined region, and a plurality of regions surrounding the predetermined region, of which each surrounding region has the same size as the predetermined region. Then, the minimum value of an absolute value of a difference ($\Delta$CD) between the line width of the predetermined region of the optical image of the pattern to be measured and the line width of the region of the reference image corresponding to the predetermined region, or the minimum value of the sum of squares of the difference ($\Delta$CD) between the line width of the predetermined region of the optical image of the pattern to be measured and the line width of the region of the reference image corresponding to the predetermined region, is obtained in every unit region. Further, in regards to regions arranged near the predetermined region, of which each region has the same size as the predetermined region, an absolute value of a difference ($\Delta$CD) between the line width of the predetermined region of the optical image of the pattern to be measured and the line width of the region of the reference image corresponding to the predetermined region becomes the minimum, or a position at which the sum of squares of the difference ($\Delta$CD) between the line width of the predetermined region of the optical image of the pattern to be measured and the line width of the region of the reference image corresponding to the predetermined region becomes the minimum, is obtained in every region. Then an average value of the minimum values of those regions, that is, the predetermined region and a plurality of regions arranged near the predetermined region, is obtained, and the average value becomes an average of $\Delta$CD in every region. A map is generated by correlating the average of $\Delta$CD and the position coordinate on the mask Ma. The unit region can be a frame, for example.

In the present embodiment the line width error is obtained based on the optical image acquired by the TDI sensor 113 for transmission and then the $\Delta$CD map is generated based on this line width error. However, the line width error can be obtained based on the optical image acquired by the TDI sensor 114 for reflection, and the $\Delta$CD map can then be generated based on this line width error. In this case, the gradation value of the optical image acquired by the TDI sensor 114 for reflection can be corrected based on the fluctuation value of the light quantity detected by the TDI sensor 113 for transmission. Further, the fluctuation of the light quantity can be detected using a part of the pixels of the TDI sensor 114 for reflection. Furthermore, in this case, the fluctuation value of the light quantity might be detected by the TDI sensor 114 for reflection, instead of the TDI sensor 113 for transmission, or by the TDI sensor 114 for reflection with the TDI sensor 113 for transmission, and then each output value of the TDI sensor 113 for transmission and the TDI sensor 114 for reflection might be corrected.

<Comparing Step (S8)>

In the comparing step S8 shown in FIG. 3, an inspection for detecting a defect of the pattern disposed in the mask Ma is performed using the optical image data of which the gradation values are corrected, and the difference image data in the comparing unit 122 shown in FIG. 1.

In the comparing unit 122, optical image data output from the gradation value correcting unit 131 is divided to the predetermined size, for example, frame data size. The reference image data output from the reference image data generating unit 121 is also divided to the frame data size corresponding to the optical image data. As mentioned below, each optical image data divided to frame data size is called optical frame data, and each reference image data divided to frame data size is called reference frame data.

As mentioned below, a defect of the optical frame data is detected by comparing optical frame data to the reference frame data in the comparing unit 122. Further, position coordinate data of the defect is generated using the measurement data, measured by the laser length measuring unit 102, in the position information unit 104.

The comparing unit 122 includes several tens of comparison parts for processing a plurality of optical frame data along with reference frame data corresponding to each optical frame data, at the same time. Next, after the processing of optical frame data is completed, each comparison part uses unprocessed optical frame data and reference frame data corresponding to unprocessed optical frame data. Thus, a large amount of optical frame data is sequentially processed as mentioned above and therefore a defect or defects will be detected.

The specific process performed by the comparing unit 122 is as follows.

Firstly, the optical frame data and the reference frame data, corresponding to the optical frame data, are output to each comparing unit as one set. Then, in the comparing unit, alignment of the reference frame data and the optical frame data (frame alignment) is performed. In this case, the optical frame data and the reference frame data are parallel shifted in a unit of a pixel (of the TDI sensor 113 for transmission and 114 for reflection), so that the position of the edge of the pattern and the position of the peak position of the brightness correspond, and the optical frame data and the reference frame data are calibrated less than a size of a unit of a pixel, by prorating the brightness of the neighboring pixel.

After finishing the alignment of the reference frame data and the optical frame data, defect detection in accordance with an appropriate comparison algorithm it is performed. For example, evaluation and the level difference between each pixel of the reference frame data and the optical frame data, and comparison of the differential value of pixels in the pattern edge direction is performed. When the difference between the reference image data and the optical image data exceeds the predetermined threshold value, that position is determined to be defective.

For example, the threshold value that is registered as a line width defect is specified in a unit of a measurement difference (nm) and measurement ratio (%) of a line width (CD: Critical Dimension) and the critical dimension ratio between the optical image data and the reference image data. Two kinds of threshold values are specified, the measurement difference of the line width is 16 nm and the measurement ratio is 8%, for example. When the pattern of the optical image data has the line width of 200 nm, if the measurement difference between optical image data and the reference image data is 20 nm, it is determined that this pattern has a defect because the value is greater than either the threshold value of the measurement difference and the threshold value of the measurement ratio.

The threshold value of the determination of a defect can be specified separately, in either the case where the line width is thicker than the reference image data, and the case where the line width is thinner than the reference image data. Further, the threshold value can be specified separately, in either the case where the width of the space between lines (the distance between patterns), instead of the line width, is thicker than the reference image data, and the case where the width of the space between the lines (the distance between the patterns), instead of the line width, is thinner than the reference image data. Further, regarding the pattern having a shape of a hole, a threshold value of the measurement of the diameter of the hole and the threshold value of the measurement ratio of the diameter of the hole can be specified. In this case, the threshold value can be specified for the cross-section of the hole along the X-direction, and a cross-section of the hole along the Y-direction, respectively.

An algorithm used for defect detection, in addition to the above-mentioned may also include, for example, a level comparison method or a differential comparison method. In the level comparison method, for example, the luminance value of the pixel in the optical frame data, namely the luminance value of the region corresponding to the pixel of the TDI sensor 113 for transmission and the TDI sensor 114 for reflection is calculated. Then, the luminance value of the reference frame data and the calculated luminance values are compared, thus, the defect is detected. In the differential comparison method, the direction along the edge of the fine pattern on the optical frame data, for example, the amount of change in the luminance value of the pixel in the direction along the edge of the line pattern is determined by differentiation. By comparing the variation of the brightness value in the change amount and the reference frame data, the defect is detected.

When the comparing unit 122 determines that the optical frame data has a defect, the defect information, such as the optical frame data, the position coordinate data of the defect information of the defect, the compared reference frame data, etc., are registered in the magnetic disk device 123.

The comparing unit 122 performs a plurality of comparison determinations while the condition of the alignment of the frame data is changing. The comparison determination includes the alignment of the frame data, defect detection, and counting the number of defect detections. The comparing unit 122 performs the comparison determination for every set of optical frame data and reference frame data, corresponding to the optical frame data, and for every comparison algorithm. The comparing unit 122 can register the defect detection result having the lowest number of defects detected by the comparison determination in the defect registration unit.

As mentioned above, the optical image data and the reference image data are sequentially input to the comparing unit 122, and a defect detection of the optical image data is performed by comparing the optical image data and the reference image data.

According to the present embodiment, the optical image of the pattern disposed in the mask Ma is acquired by the TDI sensor 113 for transmission, and the fluctuation of the light quantity of the light source 105 is detected using a part of the pixels of the TDI sensor 113 for transmission. Specifically, each pixel information in the imaging area A1 and the light quantity fluctuation detecting area A2 are obtained at the same time by the sensor elements provided along the pixel direction. Thereby, when the gradation value of the optical image acquired in the imaging area A1 is fluctuated, the fluctuation of the light quantity of the light source caused by the fluctuation of the gradation value can be obtained at approximately the same time as the acquisition of the optical image. Therefore, even if the gradation value of the optical image of the pattern disposed in the mask Ma is fluctuated by the fluctuation of the light quantity of the light source, the gradation value can be appropriately corrected, and then an accurate CD map can be obtained according to the present embodiment.

As mentioned above, the mask inspection apparatus and the mask inspection method according to the present invention are mentioned in each embodiment. However, the present invention is not limited to the mask inspection method, the mask inspection apparatus, and the mask inspection system mentioned in those embodiments. Various modifications to the present invention, improvements regarding possible combinations, and the like, may be performed. The scope of the present invention encompasses all mask inspection methods, mask inspection apparatuses, and mask inspection systems employing the elements of the present invention and variations thereof, which can be designed by those skilled in the art.

For example, as mentioned above, the fluctuation of the light quantity might be detected using a part of the pixels of the TDI sensor 114 for reflection in the present embodiment.

In the case where the fluctuation of the light quantity is detected by the TDI sensor 114 for reflection, the TDI sensor 114 for reflection includes an area (imaging area A1) for acquiring an optical image of the mask Ma, and an area (light quantity fluctuation detecting area A2) for detecting a fluctuation of the light quantity of the light source 105 as well as the TDI sensor 113 for transmission shown in FIG. 2. Specifically, the light quantity fluctuation detecting area A2 has the same length as the imaging area A1 along the integration direction that is, the direction in which a charge is accumulated, and is provided at the end of the pixel direction orthogonal to the integration direction. In this case, when the imaging area A1 becomes small, the inspection time becomes longer. Therefore, the size of the light quantity fluctuation detecting area A2 should be set so that it is large enough for detecting the fluctuation of the light quantity of the light source 105 and small enough to not increase the inspection time of the optical image in the imaging area A1.

The detection of the fluctuation of the light quantity using a part of the pixels of the TDI sensor 114 for reflection is performed in parallel with the step for acquiring the optical image of the pattern disposed in the mask Ma by the TDI sensor 114 for reflection. Therefore, the light which travels from the mirror 110 to the second light dividing unit 111, transmits through the second light dividing unit 111 and then illuminates the mask Ma, and a part of the light that is reflected by the second light dividing unit 111 and returns to the mirror 110, then enters the light quantity fluctuation detecting area A2 of the TDI sensor 114 for reflection. In order for the light, reflected by the second light dividing unit 111, to enter the TDI sensor 114 for reflection and not to the TDI sensor 113 for transmission, the arrangement of the imaging optical unit of the imaging unit can be adjusted.

According to the above-mentioned construction, when the light reflected by the second light dividing unit 111 enters the light quantity fluctuation detecting area A2 of the TDI sensor 114 for reflection, the TDI sensor 114 for reflection converts the incident light to an electronic image signal and then outputs the electronic image signal. Further, the TDI sensor 114 for reflection converts the reflected optical image of the pattern disposed in the mask Ma which enters the imaging area A1, to an image signal and outputs the image signal, at the same time. A difference between the time elapsing between when the light is emitted from the light source 105, and when the light is incident to the TDI sensor 114 for reflection after the light is reflected by the mask Ma, and the time elapsing between when the light is emitted from the light source 105, and when the light is incident to the TDI sensor 114 for reflection after the light is reflected by the second light dividing unit 111 and then is reflected by the second light dividing unit 111, is negligibly small. Therefore the fluctuation of the light quantity of the light for acquiring the optical image of the pattern disposed in the mask Ma, can be detected in real time. Further, according to the present construction, the light path of the light which enters the light quantity fluctuation detecting area A2 is approximately the same as the light path which enters the imaging area A1. Therefore, the gradation value of the optical image output at the same time as the optical image of the light quantity fluctuation detecting area A2 is corrected based on the fluctuation of the gradation value of the optical image acquired in the light quantity fluctuation detecting area A2, and then the line width of the pattern disposed in the mask Ma is measured based on the corrected optical image data. Thereby, the line width error can be accurately obtained, and further the correct ΔCD map can be obtained.

Further, the mask inspection apparatus illustrated in the embodiments includes the necessary components for these embodiments. However, the mask inspection apparatus and mask inspection system of the present invention can also include other well-known components necessary for line width error acquisition and inspection. In the present invention a "unit" can be configured by a program operating on a computer. Alternatively, the "unit" may be constructed by, not only a software program, but also a combination of software, hardware, or firmware. In the case that the "unit" may be constructed by a program, the program can be recorded in a storage unit such as a magnetic disk device.

Further features of the present invention may be summarized as follows.

According to one aspect of the present invention, a mask inspection apparatus includes an illumination optical unit, an imaging unit, a reference image data generating unit, a correcting unit, and a line width error obtaining unit. The illumination optical unit illuminates an inspection target using light emitted from a light source. The illumination optical unit includes a first light dividing unit and a second light dividing unit configured to divide the light. The first light dividing unit configured to divides the light emitted from the light source to a light path for the light to be transmitted through the inspection target, and a light path for the light to be reflected by the inspection target. The second light dividing unit divides the light, on the light path for the light to be reflected by the inspection target, in front of the inspection target. A part of the light incident to the second light dividing unit illuminates the inspection target, and another part of the light incident to the second light dividing unit is incident to the second area of the sensor without illuminating the inspection target. The imaging unit acquires optical image data of a pattern disposed in the inspection target by causing the light transmitted to the inspection target or reflected by the inspection target to be incident to a sensor. The sensor includes a first area, which the light transmitted to or reflected by the inspection target is incident to, and a second area which the light emitted from the light source, is incident to. The reference image data generating unit generates reference image data, corresponding to the optical image data, from design data of the pattern. The correcting unit acquires a gradation value of the optical image data and corrects the gradation value of the optical image data based on a fluctuation of a light quantity of the light source by obtaining a fluctuation of a gradation value of optical image data acquired using the light incident to the second area, and correcting a gradation value of optical image data acquired using the light incident to the first area. The line width error obtaining unit obtains a line width of the pattern of the corrected optical image data, and obtains a line width error which is a difference between the line width of the corrected optical image data and a line width of a pattern of the reference image data corresponding to the optical image data.

According to another aspect of the present invention, a mask inspection apparatus includes an illumination optical unit, an imaging unit, a reference image data generating unit, a correcting unit, and a line width error obtaining unit. The illumination optical unit illuminates an inspection target using light emitted from a light source. The imaging unit acquires optical image data of a pattern disposed in the inspection target by causing the light transmitted to the inspection target or reflected by the inspection target to be incident to a sensor. The sensor includes a plurality of pixels for acquiring an optical image of the pattern, and electrically stores the optical image, converts the optical image to an electric signal, and outputs the electric signal. The sensor includes a first area, which the light transmitted to or reflected by the inspection target is incident to, and a second area which the light emitted from the light source, is incident to. In the first area, a group in which prescribed pixels are arranged along a pixel direction intersecting perpendicularly to a charge accumulation direction in which a charge is accumulated is repeated. In the second area, a group in which prescribed pixels are arranged along the pixel direction is repeated with the same length as the first area along the charge accumulation direction. The reference image data generating unit generates reference image data, corresponding to the optical image data, from design data of the pattern. The correcting unit acquires a gradation value of the optical image data and corrects the gradation value of the optical image data based on a fluctuation of a light quantity of the light source by obtaining a fluctuation of a gradation value of optical image data acquired using the light incident to the second area, and correcting a gradation value of optical image data acquired using the light incident to the first area. The line width error obtaining unit obtains a line width of the pattern of the corrected optical image data, and obtains a line width error which is a difference between the line width of the corrected optical image data and a line width of a pattern of the reference image data corresponding to the optical image data.

In the above-mentioned embodiment, it is preferable that the second area is disposed at the end of the sensor in the pixel direction.

Further in the above-mentioned embodiment, it is preferable that the second area is the remaining area not used as the first area of the whole area in which the plurality of pixels are arranged in the sensor.

The above-mentioned embodiment may include a table disposed to mount the inspection target thereon, a position measuring unit disposed to measure a position coordinate of the table, and a map generating unit disposed to generate a map of the line width error corresponding to the position coordinate of the inspection target using information of the position coordinate of the table output from the position measuring unit.

The above-mentioned embodiment may also further include a comparing unit to compare the optical image data with the reference image data, and determine the existence of a defect in the case where a difference value between the optical image and the reference image is larger than a predetermined threshold value.

According to another aspect of the present invention, a mask inspection apparatus includes an illumination optical unit, an imaging unit, a reference image data generating unit, a correcting unit, and a line width error obtaining unit. The illumination optical unit illuminates an inspection target using light emitted from a light source. The imaging unit acquires optical image data of a pattern disposed in the inspection target by causing the light transmitted to the inspection target or reflected by the inspection target to be incident to a sensor. The sensor includes a first area, which the light transmitted to or reflected by the inspection target is incident to, and a second area which the light emitted from the light source, is incident to. The reference image data generating unit generates reference image data, corresponding to the optical image data, from design data of the pattern. The correcting unit acquires a gradation value of the optical image data and corrects the gradation value of the optical image data based on a fluctuation of a light quantity of the light source by obtaining a fluctuation of a gradation value of optical image data acquired using the light incident to the second area, and correcting a gradation value of optical image data acquired using the light incident to the first area by the following formula using
(1) a gradation value ($I\_img$) of the optical image data acquired using the light incident to the first area,
(2) a gradation value ($I\_sens$) of the optical image data acquired using light incident to the second area at the same time as the light incident to the first area,
(3) an initial value ($I\_sens\_hi$) of the gradation value of the optical image data acquired using the light incident to the second area under the same condition of the illumination optical unit for the acquisitions of the optical image data having the gradation value ($I\_img$) and the optical image data having the gradation value ($I\_sens$),
(4) an initial value ($I\_img\_zero$) of the gradation value of the optical image data acquired using the light incident to the first area by reducing the light quantity of the light source to zero, and
(5) an initial value ($I\_sens\_zero$) of the gradation value of the optical image data acquired using the light incident to the second area.

$$I\_corr = I\_img - I\_img\_zero \times \{(I\_sens - I\_sens\_zero)/(I\_sens\_hi - I\_sens\_zero)\} + I\_img\_zero$$

The line width error obtaining unit obtains a line width of the pattern of the corrected optical image data, and obtains a line width error which is a difference between the line width of the corrected optical image data and a line width of a pattern of the reference image data corresponding to the optical image data.

According to another aspect of the present invention, a mask inspection method includes calibrating a sensor, which electrically stores an optical image of an inspection target, converts the optical image to an electric signal, and outputs the electric signal. The sensor includes a first area in which a plurality of pixels are arranged along a pixel direction intersecting perpendicularly to a charged accumulation direction in which a charge is accumulated, and a plurality of sections of pixels are arranged along the accumulate direction, and a second area disposed with the same length as the first area at the end of the sensor in the pixel direction, in order to correspond to the characteristics of the first area of the sensor with the characteristics of the second area of the sensor. The inspection target positioned on a table is illuminated with light emitted from a light source. Optical image data of a pattern disposed in the inspection target is acquired by causing the light transmitted or reflected by the inspection target to be incident to the first area of the sensor. Optical image data is acquired by causing the light emitted from the light source, different to the light for illuminating the inspection target, to be incident to the second area. A gradation value of the optical image data acquired using the light incident to the first area by obtaining a fluctuation of a gradation value of the optical image data acquired using the light incident to the second area is corrected. Reference image data is generated corresponding to the optical image data from design data of the pattern. A line width of the pattern of the corrected optical image data is obtained. A line width error that is a difference between the line width of the corrected optical image data and a line width of the pattern of the reference image data corresponding to the optical image data is obtained.

The above-mentioned embodiment may also include measuring a position coordinate of the table, and generating a map of the line width error corresponding to the position coordinate of the inspection target using information of the position coordinate of the table.

The above-mentioned embodiment may also further include comparing the optical image data with the reference image data to determine the existence of a defect in the case where a difference value between the optical image and the reference image is larger than a predetermined threshold value.

The above-mentioned embodiment may also include the characteristics of the first area of the sensor and the characteristics of the second area of the sensor being gain characteristics and offset characteristics respectively.

According to another aspect of the present invention, a mask inspection method includes calibrating a sensor, which electrically stores an optical image of an inspection target, converts the optical image to an electric signal, and outputs the electric signal. The sensor includes a first area in which a plurality of pixels are arranged along a pixel direction intersecting perpendicularly to a charged accumulation direction in which a charge is accumulated, and a plurality of sections of pixels are arranged along the accumulate direction, and a second area disposed with the same length as the first area at the end of the sensor in the pixel direction, in order to correspond to the characteristics of the first area of the sensor with the characteristics of the second area of the sensor. The inspection target positioned on a table is illuminated with light emitted from a light source. Optical image data of a pattern disposed in the inspection target is acquired by causing the light transmitted or reflected by the inspection target to be incident to the first area of the sensor. Optical image data is acquired by causing the light emitted from the light source, different to the light for illuminating the inspection target, to be incident to the second area. A gradation value of the optical image data acquired using the light incident to the first area by obtaining a fluctuation of a gradation value of the optical image data acquired using the light incident to the second area is corrected by the following formula using (1) a gradation value ($I\_img$) of the optical image data acquired using the light incident to the first area,
(2) a gradation value ($I\_sens$) of the optical image data acquired using light incident to the second area at the same time as the light incident to the first area,
(3) an initial value ($I\_sens\_hi$) of the gradation value of the optical image data acquired using the light incident to the second area under the same condition of the illumination optical unit for the acquisitions of the optical image data having the gradation value ($I\_img$) and the optical image data having the gradation value ($I\_sens$),
(4) an initial value ($I\_img\_zero$) of the gradation value of the optical image data acquired using the light incident to the first area by reducing the light quantity of the light source to zero, and
(5) an initial value ($I\_sens\_zero$) of the gradation value of the optical image data acquired using the light incident to the second area.

$$I\_corr = I\_img - I\_img\_zero \times \{(I\_sens - I\_sens\_zero)/(I\_sens\_hi - I\_sens\_zero)\} + I\_img\_zero.$$

What is claimed is:

1. A mask inspection apparatus comprising:
an illumination optical unit configured to illuminate an inspection target using light emitted from a light source;
an imaging unit configured to acquire optical image data of a pattern disposed in the inspection target by causing the light transmitted through the inspection target or reflected by the inspection target to be incident to a sensor, wherein the sensor includes a first area upon which the light transmitted through or reflected by the inspection target is incident to acquire the optical image data of the pattern, and a second area upon which the light emitted from the light source is incident to detect a light quantity of the light source, the first and second areas are independent areas that output a respective (1) optical image data of the pattern and (2) a detected light quantity of the light source;
a reference image data generating unit configured to generate reference image data, corresponding to the optical image data, from design data of the pattern;
a correcting unit configured to acquire a gradation value of the optical image data, and to correct the acquired gradation value of the optical image data based on a fluctuation of the light quantity of the light source by obtaining a fluctuation of a gradation value of optical image data acquired using the light from the light source incident upon the second area; and
a line width error obtaining unit configured to obtain a line width of the pattern of the corrected optical image data, and obtain a line width error which is a difference between the line width of the corrected optical image data and a line width of a pattern of the reference image data corresponding to the optical image data.

2. The mask inspection apparatus according to claim 1, wherein the illumination optical unit comprises a first light dividing unit configured to divide the light emitted from the light source to a light path for the light to be transmitted through the inspection target, and a light path for the light to be reflected by the inspection target; and
a second light dividing unit configured to divide the light, on the light path for the light to be reflected by the inspection target, in front of the inspection target; and
wherein a part of the light to be incident to the second light dividing unit illuminates the inspection target, and another part of the light incident to the second light dividing unit is incident to the second area of the sensor without illuminating the inspection target.

3. The mask inspection apparatus according to claim 1, wherein the sensor includes a plurality of pixels for acquiring an optical image of the pattern, electrically stores the optical image, converts the optical image to an electric signal, and outputs the electric signal;
wherein in the first area, a group in which prescribed pixels are arranged along a pixel direction intersecting perpendicularly to a charge accumulation direction in which a charge is accumulated, is repeated; and
wherein in the second area, a group in which prescribed pixels are arranged along the pixel direction, is repeated with the same length as the first area along the charge accumulation direction.

4. The mask inspection apparatus according to claim 3, wherein the second area is disposed at the end of the sensor in the pixel direction.

5. The mask inspection apparatus according to claim 3, wherein the second area is the remaining area not used as the first area of the whole area in which the plurality of pixels are arranged in the sensor.

6. The mask inspection apparatus according to claim 2, wherein the sensor includes a plurality of pixels for acquiring an optical image of the pattern, electrically stores the optical image, converts the optical image to an electric signal, and outputs the electric signal;
wherein in the first area, a group in which prescribed pixels are arranged along a pixel direction intersecting perpendicularly to a charge accumulation direction in which a charge is accumulated, is repeated; and
wherein in the second area, a group in which prescribed pixels are arranged along the pixel direction, is repeated with the same length as the first area along the charge accumulation direction.

7. The mask inspection apparatus according to claim 6, wherein the second area is disposed at the end of the sensor in the pixel direction.

8. The mask inspection apparatus according to claim 6, wherein the second area is the remaining area not used as the first area of the whole area in which the plurality of pixels area arranged in the sensor.

9. The mask inspection apparatus according to claim 1, wherein the correcting unit obtains a corrected value ($I\_corr$) of a gradation value of the optical image data acquired using light incident to the first area by the following formula using (1) a gradation value ($I\_img$) of the optical image data acquired using the light incident to the first area,
(2) a gradation value ($I\_sens$) of the optical image data acquired using light incident to the second area at the same time as the light incident to the first area,
(3) an initial value ($I\_sens\_hi$) of the gradation value of the optical image data acquired using the light incident to the second area under the same condition of the illumination optical unit for the acquisitions of the optical image data having the gradation value (I_img) and the optical image data having the gradation value (I_sens), (4) an initial value (I_img_zero) of the gradation value of the optical image data acquired using the light incident to the first area by reducing the light quantity of the light source to zero, and (5) an initial value (I_sens_zero) of the gradation value of the optical image data acquired using the light incident to the second area.

$$I\_corr = I\_img - I\_img\_zero \times \{(I\_sens - I\_sens\_zero)/(I\_sens\_hi - I\_sens\_zero)\} + I\_img\_zero.$$

10. The mask inspection apparatus according to claim 1, further comprising:

a table configured to mount the inspection target thereon;

a position measuring unit configured to measure a position coordinate of the table;

a map generating unit configured to generate a map of the line width error corresponding to the position coordinate of the inspection target using information of the position coordinate of the table output from the position measuring unit.

11. The mask inspection apparatus according to claim 2, further comprising:

a table configured to mount the inspection target thereon;

a position measuring unit configured to measure a position coordinate of the table;

a map generating unit configured to generate a map of the line width error, using information of the position coordinate of the table output from the position measuring unit, corresponding to the position coordinate of the inspection target.

12. The mask inspection apparatus according to claim 10, further comprising a comparing unit configured to compare the optical image data with the reference image data, and determine the existence of a defect in the case where a difference value between the optical image and the reference image is larger than a predetermined threshold value.

13. The mask inspection apparatus according to claim 11, further comprising a comparing unit configured to compare the optical image data with the reference image data, and determine the existence of a defect in the case where a difference value between the optical image and the reference image is larger than a predetermined threshold value.

* * * * *